United States Patent
Schurzig (12)

(10) Patent No.: US 10,953,226 B2
(45) Date of Patent: Mar. 23, 2021

(54) FULL POSTOPERATIVE INSERTION OF PARTIALLY INSERTED COCHLEAR IMPLANTS

(71) Applicant: MED-EL Elektromedizinische Geraete GmbH, Innsbruck (AT)

(72) Inventor: Daniel Schurzig, Hannover (DE)

(73) Assignee: MED-EL Elektromedizinische Geraete GmbH, Innsbruck (AT)

( * ) Notice: Subject to any disclaimer, the term of this patent is extended or adjusted under 35 U.S.C. 154(b) by 132 days.

(21) Appl. No.: 16/327,927

(22) PCT Filed: Sep. 12, 2017

(86) PCT No.: PCT/US2017/051051
§ 371 (c)(1),
(2) Date: Feb. 25, 2019

(87) PCT Pub. No.: WO2018/052867
PCT Pub. Date: Mar. 22, 2018

(65) Prior Publication Data
US 2019/0224482 A1 Jul. 25, 2019

Related U.S. Application Data
(60) Provisional application No. 62/394,789, filed on Sep. 15, 2016.

(51) Int. Cl.
*A61N 1/36* (2006.01)
*A61N 1/05* (2006.01)
(Continued)

(52) U.S. Cl.
CPC ...... *A61N 1/36039* (2017.08); *A61B 17/3468* (2013.01); *A61M 31/00* (2013.01); *A61N 1/0541* (2013.01); *A61N 1/36038* (2017.08)

(58) Field of Classification Search
CPC ............ A61N 1/36039; A61N 1/36038; A61N 1/0541; A61B 17/3468; A61M 31/00;
(Continued)

(56) References Cited

U.S. PATENT DOCUMENTS

| 7,050,858 B1 | 5/2006 | Kuzma et al. |
| 2005/0006009 A1* | 1/2005 | Esashi ............... A61M 25/0138 148/518 |

(Continued)

FOREIGN PATENT DOCUMENTS

| CN | 1258826 A | 7/2000 |
| CN | 103347465 A | 10/2013 |

(Continued)

OTHER PUBLICATIONS

International Searching Authority/U.S. International Search Report and Written Opinion of the International Searching Authority, Application No. PCT/US2017/051051, dated Nov. 17, 2017, 16 pages.

(Continued)

*Primary Examiner* — Katrina M Stransky
(74) *Attorney, Agent, or Firm* — Sunstein LLP (57) ABSTRACT

An implantable electrode arrangement for a cochlear implant system is described. The arrangement includes an electrode array with an outer surface having electrode contacts to apply cochlear stimulation signals to target neural tissue within an implanted patient cochlea. An electrode lead delivers the cochlear stimulation signals from an implanted signal processor to the electrode array. An electrode transition section includes a distal end portion of the electrode lead that is connected to a basal end portion of the electrode array. An electrode storage device contains the electrode transition section and is secured at an electrode opening in an outer surface of the patient cochlea. The electrode storage
(Continued)

device is controllable after being surgically implanted to further insert an additional section of the electrode array from the electrode storage device into the patient cochlea and thereby implant a greater portion of the electrode array more deeply into the patient cochlea.

9 Claims, 9 Drawing Sheets

(51) Int. Cl.
*A61M 31/00* (2006.01)
*A61B 17/34* (2006.01)

(58) Field of Classification Search
CPC ... A61M 25/0138; A61F 11/04; A61F 11/045; A61F 11/00
See application file for complete search history.

(56) References Cited

U.S. PATENT DOCUMENTS

2008/0077221 A1* 3/2008 Milojevic ............ A61N 1/0541
607/137

| | | |
|---|---|---|
| 2011/0066160 A1 | 3/2011 | Simaan et al. |
| 2012/0071890 A1 | 3/2012 | Taylor et al. |
| 2012/0191161 A1 | 7/2012 | Van Dijk |
| 2014/0018736 A1 | 1/2014 | Hessler |
| 2015/0119967 A1 | 4/2015 | Pawsey et al. |

FOREIGN PATENT DOCUMENTS

| | | |
|---|---|---|
| CN | 104519926 A | 4/2015 |
| CN | 105813604 A | 7/2016 |
| EP | 2 113 283 A1 | 11/2009 |
| WO | WO 2018/052867 A1 * | 3/2018 |

OTHER PUBLICATIONS

European Patent Office Extended European Search Report, Application No. 17851384.2, dated Jun. 9, 2020, 6 pages.
China National Intellectual Property Administration Office Action, Application No. 201780055862.6, dated May 7, 2020, 9 pages.
Australian Patent Office Examination Report No. 1, Application No. 2017327851, dated Apr. 24, 2019, 4 pages.

* cited by examiner

FULL POSTOPERATIVE INSERTION OF PARTIALLY INSERTED COCHLEAR IMPLANTS

This application is a 371 national phase entry of Patent Cooperation Treaty Application PCT/US2017/051051, filed Sep. 12, 2017, which in turn claims priority from U.S. Provisional Patent Application 62/394,789, filed Sep. 15, 2016, both of which are incorporated herein by reference in their entireties.

TECHNICAL FIELD

The present invention relates to medical implants, and more specifically to an implantable electrode arrangement for cochlear implant systems.

BACKGROUND ART

Figure 1:
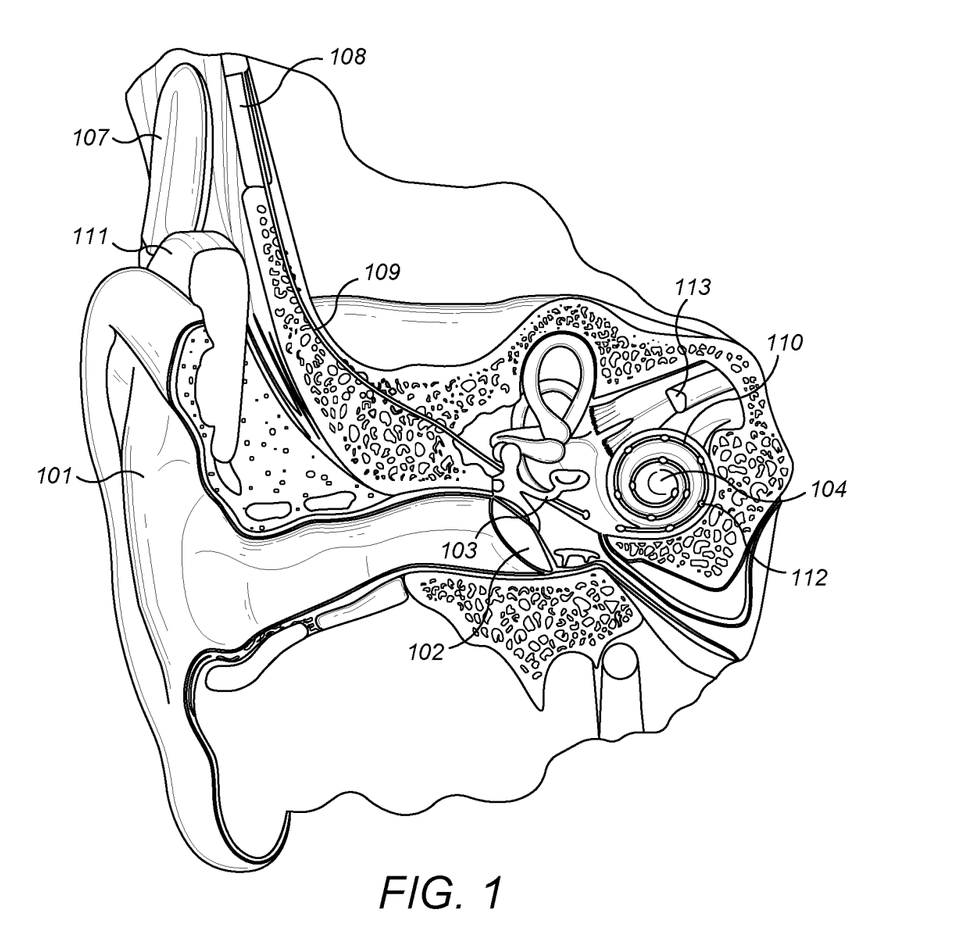
FIG. 1 shows various anatomical structures in a human ear and some components of a typical cochlear implant system.

A normal ear transmits sounds as shown in FIG. 1 through the outer ear 101 to the tympanic membrane (eardrum) 102, which moves the bones of the middle ear 103, which in turn vibrate the oval window and round window openings of the cochlea 104. The cochlea 104 is a long narrow duct wound spirally about its axis for approximately two and a half turns. The cochlea 104 includes an upper channel known as the scala vestibuli and a lower channel known as the scala tympani, which are connected by the cochlear duct. The scala tympani forms an upright spiraling cone with a center called the modiolus where the spiral ganglion cells of the auditory nerve 113 reside. In response to received sounds transmitted by the middle ear 103, the fluid filled cochlea 104 functions as a transducer to generate electric pulses that are transmitted to the cochlear nerve 113, and ultimately to the brain. Hearing is impaired when there are problems in the ability to transduce external sounds into meaningful action potentials along the neural substrate of the cochlea 104.

In some cases, hearing impairment can be addressed by an auditory prosthesis system such as a cochlear implant that electrically stimulates auditory nerve tissue with small currents delivered by multiple electrode contacts distributed along an implant electrode. FIG. 1 shows some components of a typical cochlear implant system where an external microphone provides an audio signal input to an external signal processing stage 111 which implements one of various known signal processing schemes. The processed signal is converted by the external signal processing stage 111 into a digital data format, such as a sequence of data frames, for transmission into a receiver processor in an implant housing 108. Besides extracting the audio information, the receiver processor in the implant housing 108 may perform additional signal processing such as error correction, pulse formation, etc., and produces a stimulation pattern (based on the extracted audio information) that is sent through an electrode lead 109 to an implanted electrode array 110 which penetrates into the cochlea 104 through a surgically made electrode opening in the outer surface of the cochlea 104. Such an electrode opening—as used throughout this description—in the outer surface of the cochlear is made during surgery, for example with an incision as commonly known from electrode insertion techniques through round-window or cochleostomy. Typically, this electrode array 110 includes multiple electrode contacts 112 on its surface that deliver the stimulation signals to adjacent neural tissue of the cochlea 104 which the brain of the patient interprets as sound. The individual electrode contacts 112 may be activated sequentially, or simultaneously in one or more contact groups.

Some patients with hearing loss still retain some amount of residual hearing. Many such patients can benefit from the simultaneous employment of a cochlear implant and a conventional mechanical hearing aid, often referred to as an electroacoustic stimulation (EAS) system. See A. Illg, A. Buchner, O. Majdani, T. Lenarz, "Sprachverstehen in Ruhe und im Geräusch bei unterschiedlichen Elektrodenlängen", presented at the 19th annual meeting of the Deutsche Gesellschaft für Audiologie e.V., Hannover, Germany, 2016; See Büchner et al., "Impact of low-frequency hearing," Audiology and Neurotology, 14. Suppl. 1 (2009): 8-13; Von Ilberg et al. "Electric-acoustic stimulation of the auditory system: a review of the first decade," Audiology and Neurotology, 16. Suppl. 2 (2011): 1-30 (all three incorporated herein by reference in their entireties). EAS candidates who still show residual hearing are typically treated with a shorter electrode array because the residual hearing abilities are usually in the low frequency region—the apical region of the cochlea—and shorter electrode arrays are less likely to damage the intracochlear structures or influence the mechanical characteristics of the cochlea. On the other hand, patients with little or no residual hearing usually are better treated with longer electrode arrays which can provide electrical stimulation to a larger portion of the cochlea, thereby significantly improving speech understanding as can be seen in FIG. 2A.

Figure 2A:
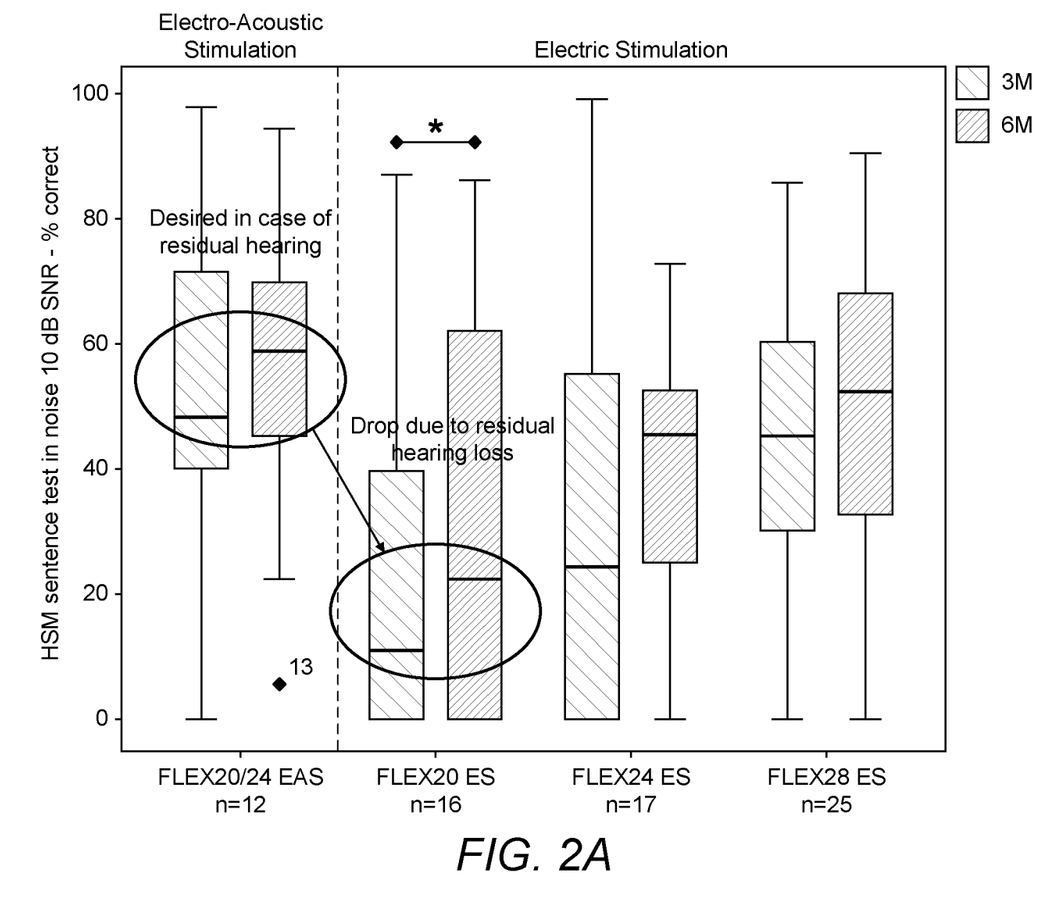
FIGS. 2A-2B show speech understanding data for different length cochlear implant electrode arrays.

Unfortunately, as FIG. 2A also shows, some patients lose their residual hearing during or after cochlear implantation. Obviously this is a problem because, among other things, such patients should be treated by a long electrode array, but are already implanted with a short one. The benefit of a cochlear implant for such patients is lower than what could have been achieved with a longer electrode array—the patient either has to deal with reduced speech perception or undergo re-implantation with a longer electrode array.

SUMMARY

Embodiments of the present invention are directed to an implantable electrode arrangement for a cochlear implant system. The arrangement includes an electrode array with an outer surface having multiple electrode contacts configured for applying cochlear stimulation signals to target neural tissue within an implanted patient cochlea. An electrode lead is configured for delivering the cochlear stimulation signals from an implanted signal processor to the electrode array. An electrode transition section includes a distal end portion of the electrode lead connected to a basal end portion of the electrode array. An electrode storage device is configured to contain the electrode transition section and to be secured at an electrode opening in an outer surface of the patient cochlea. The electrode arrangement is configured for a portion of the electrode array to be surgically implanted through the electrode opening into the patient cochlea so that the electrode transition section remains within the electrode storage device secured outside the patient cochlea. After being surgically implanted, the electrode storage device is configured to be controllable to further insert an additional section of the electrode array from the electrode storage device into the patient cochlea and thereby implant a greater portion of the electrode array more deeply into the patient cochlea.

In some further specific embodiments, the electrode storage device may specifically include one or more shape memory alloy (SMA) components configured to further insert the additional section of the electrode array; for example, in the form of a spring element and/or one or more wire filaments made of SMA material. The electrode storage device may use a guide tube that contains a slidable sleeve secured to an outer surface of the electrode transition section.

The additional section of the electrode array may comprise some or all of the electrode array contained within the electrode storage device. The electrode storage device may be configured to be controllable after being surgically implanted to further insert a plurality of additional sections of the electrode array from the electrode storage device into the patient cochlea in a sequence of incremental steps.

Embodiments of the present invention also include a cochlear implant system having an electrode arrangement according to any of the foregoing.

DETAILED DESCRIPTION

Figure 2B:
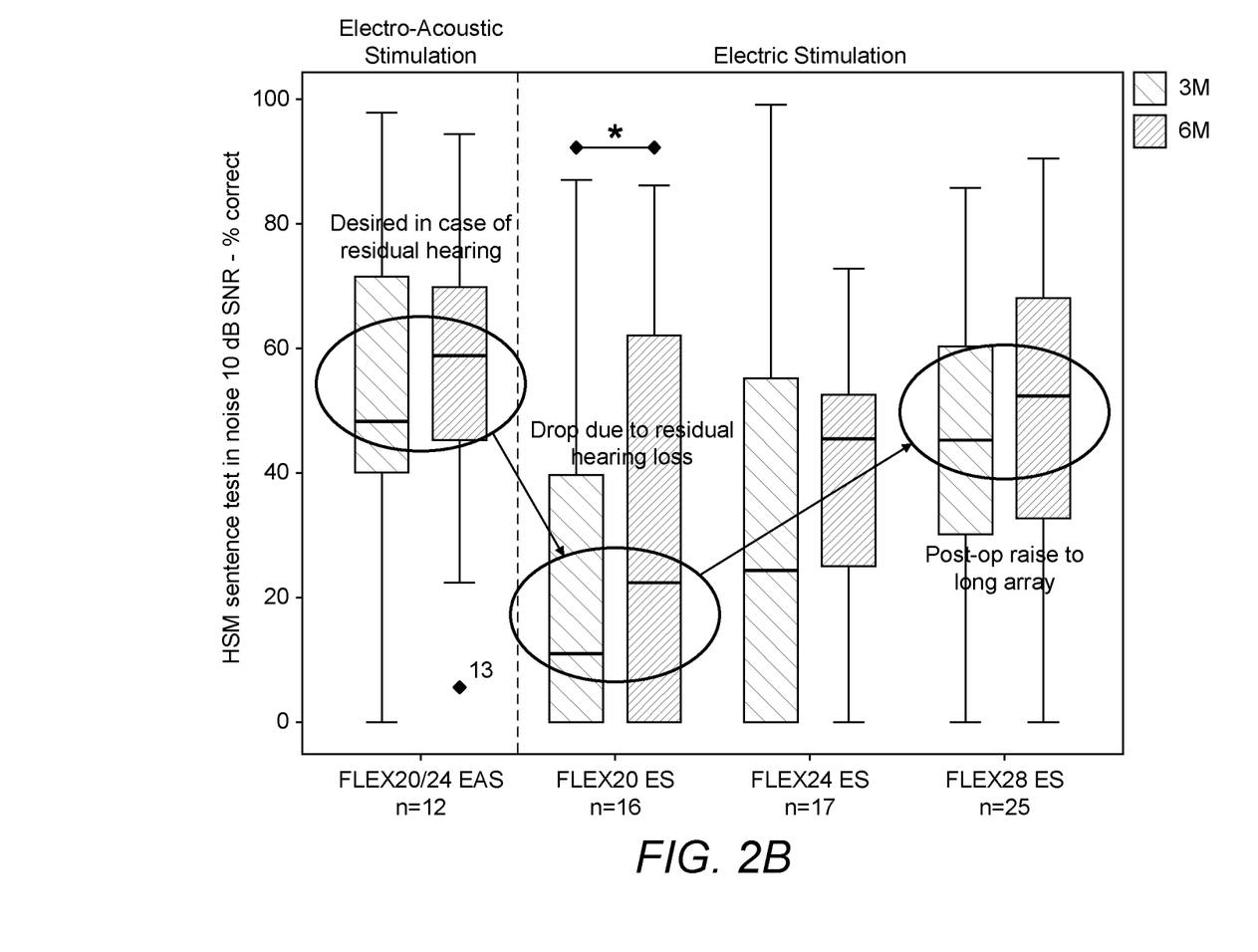

Patients with sufficient preoperative residual hearing should have a short electrode array inserted into the cochlea. In the unfortunate cases where the patients postoperatively loses their residual hearing, embodiments of the present invention than convert the short electrode array into a long one without additional surgery. For example, the right side of FIG. 2B shows the potential increase in speech understanding if a 20 mm array is postoperatively increased to 28 mm. By providing a mechanism for such postoperative full (or further) insertion of a partially inserted electrode array without additional surgery, implantation patients can avoid reduced speech perception due to an unnecessarily short electrode array.

Figure 3:
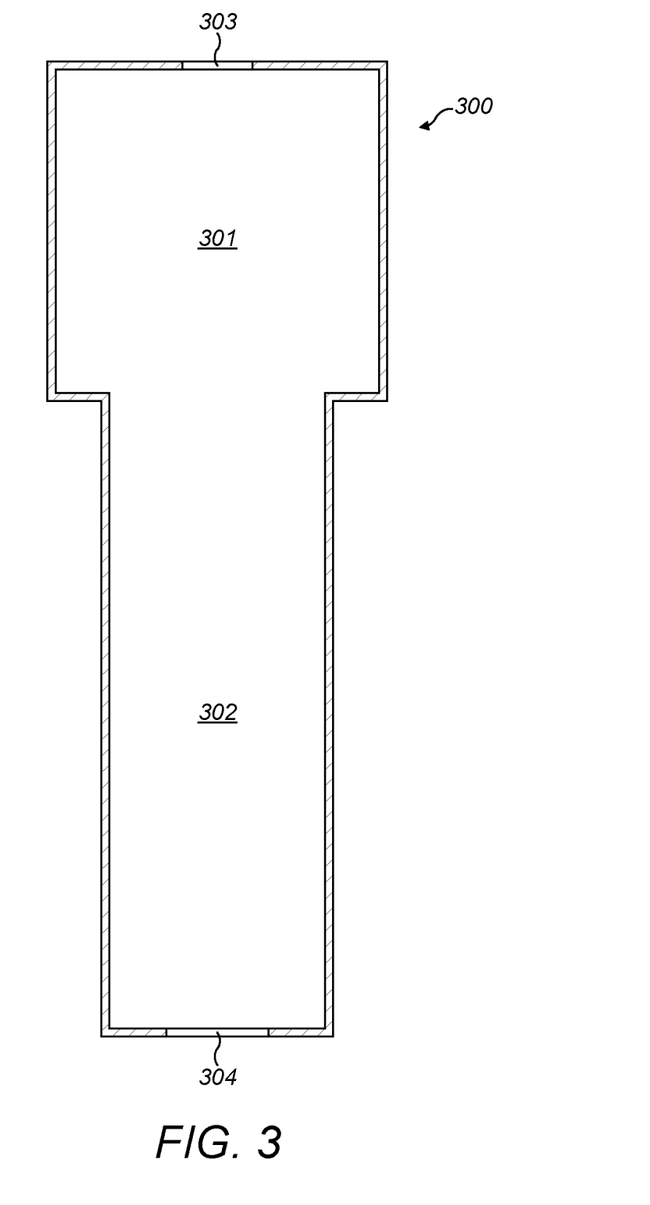
FIG. 3 shows basic structural features of an electrode storage device according to an embodiment of the present invention.

One such arrangement for an electrode storage device for a cochlear implant system is shown in FIG. 3. The electrode storage device 300 is configured to contain an electrode transition section of a cochlear implant electrode that includes a distal end portion of the electrode lead connected to a basal end portion of the electrode array. Specifically, a lead storage chamber 301 contains the electrode lead portion of the transition section, which enters the lead storage chamber 301 via a lead opening 303. An array storage chamber 302 contains the electrode array portion of the transition section, which exits the array storage chamber 302 via an array opening 304.

The electrode storage device 300 may specifically be cylindrically shaped, and can be formed from two matching half-cylinders. The electrode storage device 300 isolates an internal array insertion mechanism from the surrounding tissue to prevent undesired interactions between the two, and also provides a length of available electrode lead which will remain unaffected by tissue growth (i.e. cannot get stuck). As explained above, the electrode storage device 300 enables additional postoperative insertion of a partially inserted, long electrode array; for example, a partially inserted FLEX28 electrode produced by MED-EL Elektromedizinische Geräte Gesellschaft m.b.H. Preferably, the electrode transition section is placed into the electrode storage device 300 prior to surgery so that that initial short section of the electrode array (e.g. the final 16 mm of a FLEX28 electrode) protrudes from the array opening 304, while the remaining portion of the electrode array (e.g., the remaining 12 mm of a FLEX28 electrode) is stored within the array storage chamber 302.

The electrode storage device 300 is adapted to be fixedly secured after implantation surgery at an electrode opening in an outer surface of the patient cochlea within the tympanic cavity. It is especially important for the electrode storage device 300 to remain fixed in place when the postoperative array insertion mechanism is activated to further insert more of the electrode array into the cochlea. For example, the electrode storage device 300 can be fixed by using bone cement and/or additional securing features such as screws or clips on the outside of the electrode storage device 300 which anchor the device to anatomical features of the patient (e.g. at the posterior tympanotomy).

Figure 4A:
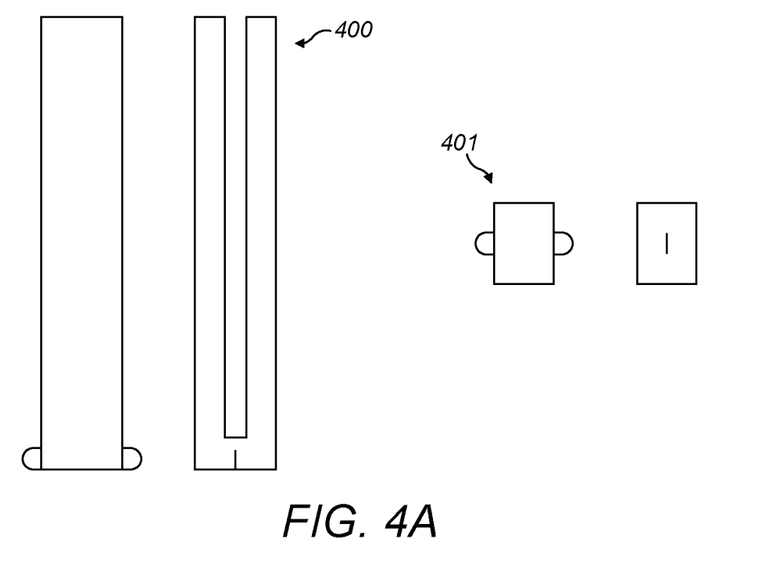
FIGS. 4A-4B show structural features of a guide tube and slider for use within an electrode storage device according to an embodiment of the present invention.
Figure 4B:
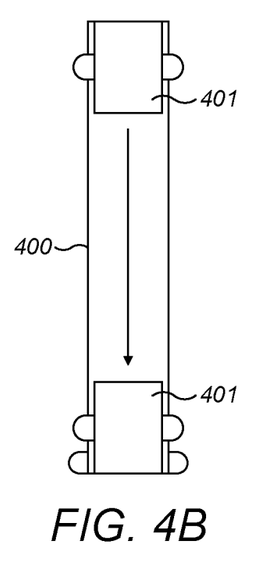

The electrode storage device 300 contains an internal array insertion mechanism as shown in FIGS. 4A-4B with a slotted guide tube 400 and a slidable array sleeve 401 that is fixated to the electrode array 110. The array sleeve 401 can freely move within and along the guide tube 400. Thus there is a clearance between the inner diameter of the guide tube 400 and the outer diameter of the sleeve 401. The inner diameter of the sleeve 401 matches the outer diameter of the electrode array so that the latter fits snugly within the sleeve 401 to support fixation of the array sleeve 401 to the electrode array 110. One or more bails on the outside of the sleeve 401 fit into the slot in the guide tube 400 to prevent relative rotation between the two components.

Figure 5A:
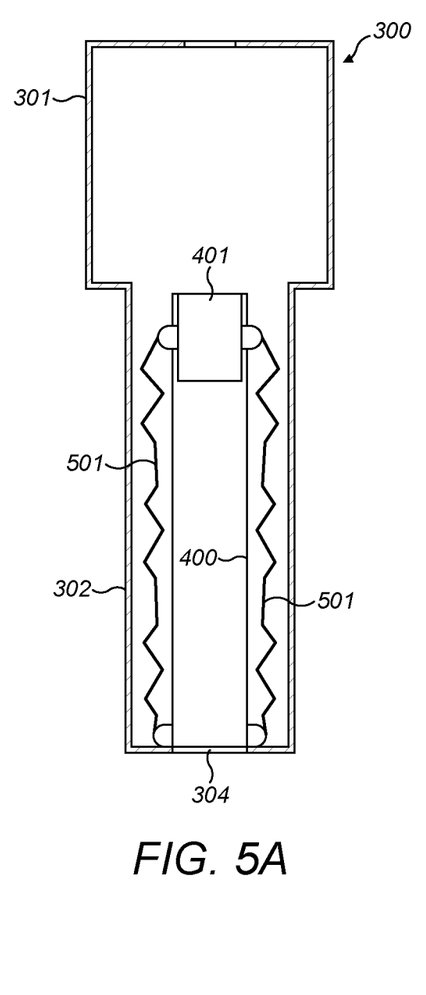
FIGS. 5A-5B show the principles of operation of an electrode storage device according to an embodiment of the present invention.
Figure 5B:
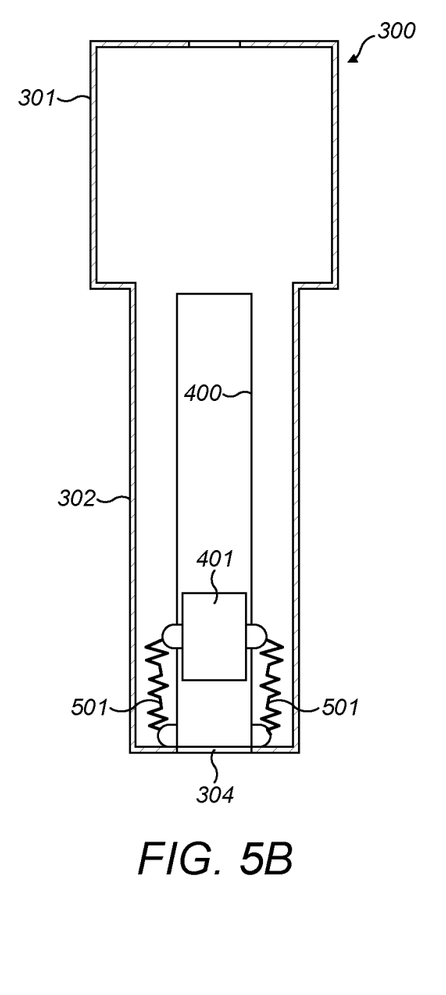

To controllably operate the array insertion mechanism, one or more shape memory alloy (SMA) components 501 form an insertion element, as shown in FIGS. 5A-5B, that connects the outer bail of the array sleeve 401 to the interior of the array storage chamber 302 near the array opening 304. FIG. 5A shows the configuration of the electrode storage device 300 initially after surgery that partially implants a shorter section of a longer electrode array—the array sleeve 401 is fully drawn back into the interior of the electrode storage device 300 and the SMA components 501 are fully extended out of their "memorized" shape into an elongated profile. At some later time after surgery, the array insertion mechanism can be activated by selectively applying an activation voltage to the SMA components 501 (see FIG. 6A) to cause them to contract, as shown in FIG. 5B, to draw the array sleeve 401 towards the array opening 304, pushing the stored portion of the electrode array out through the opening to insert the electrode array further into the patient cochlea.

SMA components 501 are desirable in this application because of their small size and the limited space that is available within the tympanic cavity. Furthermore, the SMA components 501 experience a change in their electrical resistance as they deform back to their memorized shape, which can be used as a measurement parameter to monitor the insertion process. The SMA components 501 may be wire filaments made of SMA material and the array insertion mechanism may utilize one or more SMA components 501 equally spaced around the array sleeve 401. Each of these SMA components 501 may be individually contractible and causes a contraction force onto the electrode array via the array sleeve 401. For example an array sleeve 401 may have eight equally spaced such SMA components 501, and if only four of these are contracted, then the force applied to the electrode array is four times the force of when only one SMA component 501 is contracted and half of the force as if all eight SMA components 501 are contracted. This controllable selective activation of the SMA components 501 allows controlling the insertion force applied to the electrode array. This in turn helps avoid structural damage to the cochlea by the electrode array due too to excessive applied force.

Figure 6A:
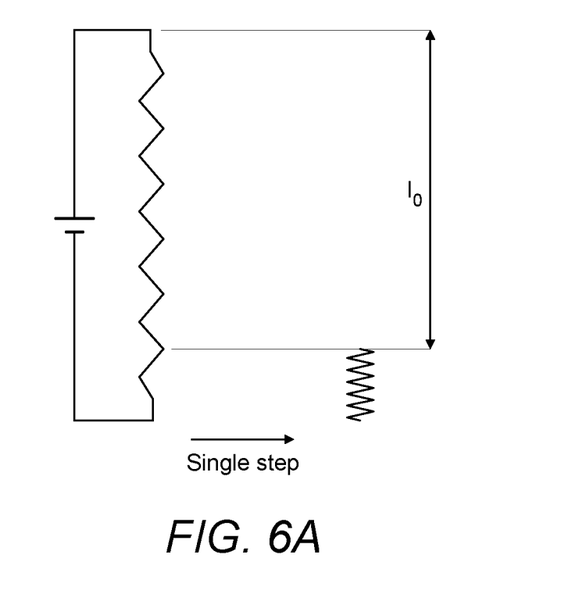
FIGS. 6A-6B show equivalent electrical circuits for shape memory alloy components according to an embodiment of the present invention.
Figure 6B:
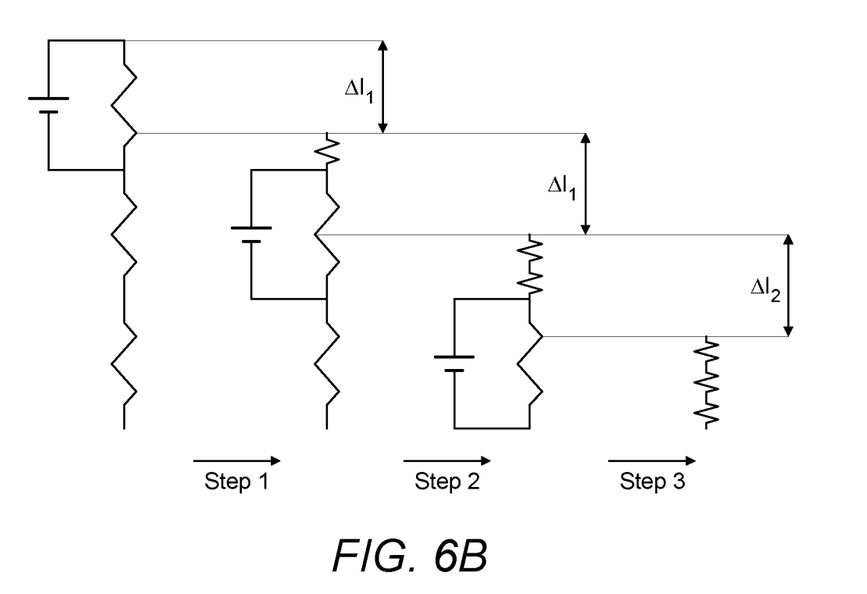

If the goal of the postoperative repositioning of the electrode array is a full insertion of the stored portion of the array, then a single SMA component 501 may be sufficient to insert the array an additional $l_0$ as shown in FIG. 6A. In some embodiments, it may be useful if the storage device 301 is configured to be controllable after being surgically implanted to further insert multiple additional sections of the electrode array into the patient cochlea in a sequence of incremental steps, as shown in FIG. 6B. A serial composition can be used with the number n of SMA components 501 corresponding to the desired number of incremental steps. The specific distance of a postoperative incremental insertion $\Delta l_i$ performed by an SMA component 501 depends on the material and geometry of the component itself, i.e. its length before and after it was actuated.

Figure 7A:
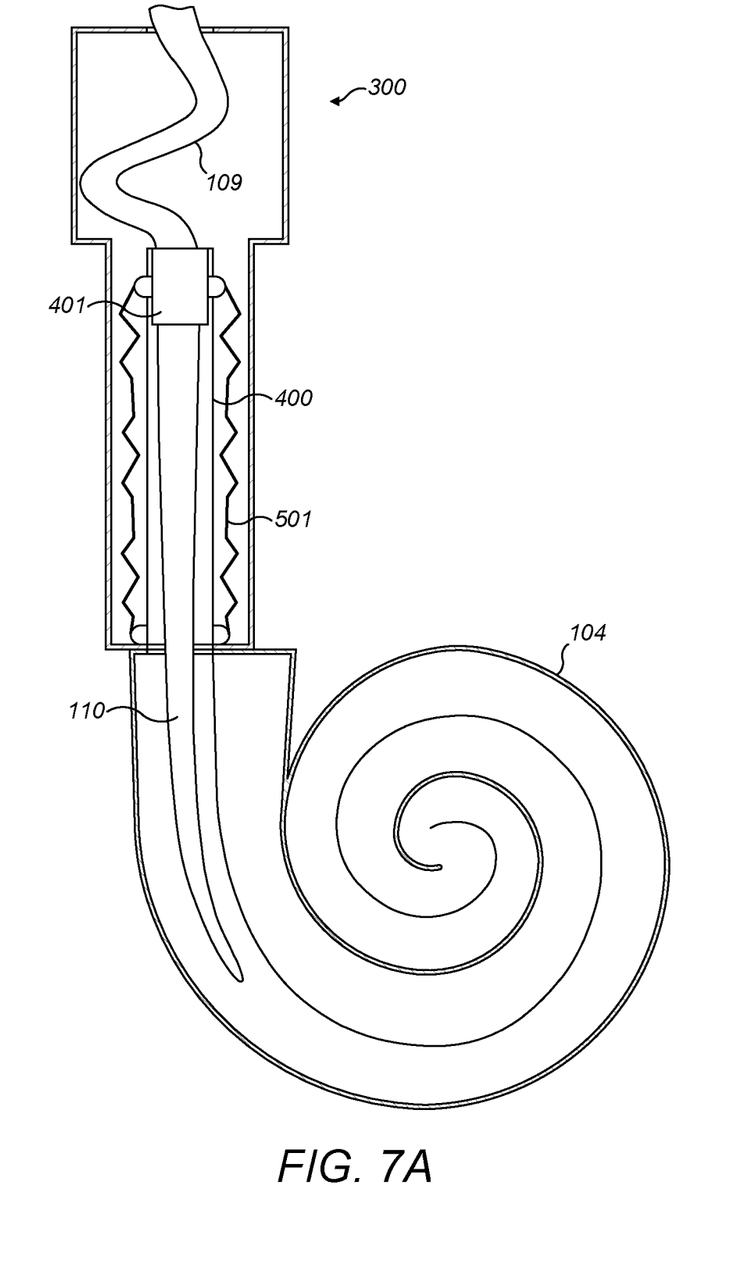
FIG. 7A-7B show use of an electrode storage device for post-surgical further insertion of an implanted electrode array according to an embodiment of the present invention.
Figure 7B:
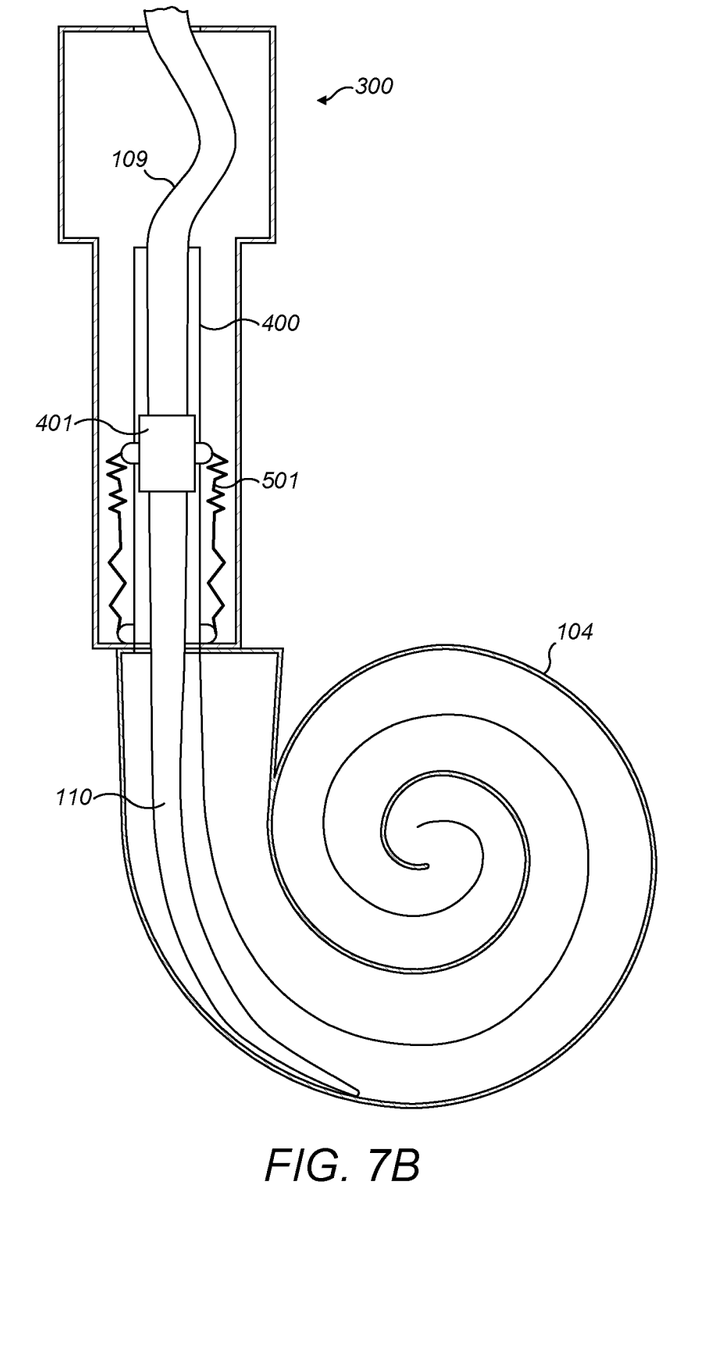

FIG. 7A-7B show use of an electrode storage device for post-surgical further insertion of an implanted electrode arrangement for a cochlear implant system according to an embodiment of the present invention. Specifically, FIGS. 7A-7B show the various structures discussed above in the specific context of a cochlear implant electrode and an implanted patient cochlea. So a conventional long electrode array 110 (e.g. a FLEX28 electrode array) has an outer surface with multiple electrode contacts configured for applying cochlear stimulation signals to target neural tissue within an implanted patient cochlea 104. And a corresponding electrode lead 109 is configured for delivering the cochlear stimulation signals from the implanted signal processor 108 to the electrode array 110. An electrode storage device 300 is configured to be secured at an electrode opening in an outer surface of the patient cochlea 104 and contains an electrode transition section that includes a distal end portion of the electrode array 110 connected to a basal end portion of the electrode array 110. FIG. 7A shows that a portion of the electrode array 110 (e.g. 16 mm) initially is surgically implanted through the electrode opening into a portion of the patient cochlea 104 so that the electrode transition section remains within the electrode storage device 300 secured outside the patient cochlea 104.

After implantation, the patient can then be treated as an EAS patient, meaning that a mechanical hearing aid can be used to provide stimulation for the patient's residual hearing (low frequency sounds) that supplements the electrical stimulation signals from the implanted portion of the electrode array 110 (high frequency sounds). A cochlear implant system is typically activated about one month after surgery. At the activation fitting appointment or any time later in life when it is determined that the patient's residual hearing has been lost, the implanted processor 108 can activate the SMA components 501 to further insert an additional section of the electrode array 110 from the electrode storage device 300 into the patient cochlea 104 and thereby implant a greater portion of the electrode array 110 more deeply into the patient cochlea 104, extending the frequency range that is handled by electrical stimulation and improving the speech perception of the patient without additional surgery.

How many of the SMA components 501 to activate may depend on the patient's audiogram. The additional postoperative insertion of the electrode array 110 ideally should be just into the part of the cochlea 104 where residual hearing is not present and not covered by existing electrical stimulation, while leaving undisturbed any more apical portion of the cochlea 104 that still retains residual hearing.

Alternatively to the SMA components 501, an embodiment of the invention could use preloaded insertion springs to provide the desired postoperative insertion of the additional portion of the electrode array 110. However, in that case the force generated by the spring at the beginning of the insertion is the highest and decreases as the electrode array 110 moves forward. Hence, this alternative approach may create an abrupt and sudden insertion velocity which could potentially harm the resulting intact intracochlear structures. In contrast thereto, the SMA components 501 should create a smooth and slow insertion velocity which can be influenced by the voltage applied.

Although various exemplary embodiments of the invention have been disclosed, it should be apparent to those skilled in the art that various changes and modifications can be made which will achieve some of the advantages of the invention without departing from the true scope of the invention.

What is claimed is:

1. An electrode arrangement for an implantable cochlear implant system, the arrangement comprising:
    an electrode array with an outer surface having a plurality of electrode contacts configured for applying cochlear stimulation signals to target neural tissue within an implanted patient cochlea;
    an electrode lead configured for delivering the cochlear stimulation signals from an implanted signal processor to the electrode array;
    an electrode transition section comprising a distal end portion of the electrode lead connected to a basal end portion of the electrode array; and
    an electrode storage device configured to contain the electrode transition section and configured to be secured at an electrode opening in an outer surface of the patient cochlea;
    wherein the electrode arrangement as a whole is implantable, and is configured to be initially surgically implanted with a portion of the electrode array extending through the electrode opening into the patient cochlea and the electrode transition section remaining within the electrode storage device secured outside the patient cochlea; and
    wherein the electrode storage device is configured to be controllable subsequent to being surgically implanted, to further insert an additional section of the electrode array from the electrode storage device into the patient cochlea and thereby implant a greater portion of the electrode array more deeply into the patient cochlea.

2. The electrode arrangement according to claim 1, wherein the electrode storage device includes one or more shape memory alloy (SMA) components configured to further insert the additional section of the electrode array.

3. The electrode arrangement according to claim 2, wherein the one or more SMA components comprise a spring element.

4. The electrode arrangement according to claim 2, wherein the one or more SMA components comprise one or more wire filaments made of SMA material.

5. The electrode arrangement according to claim 1, wherein the electrode storage device comprises a guide tube containing a slidable sleeve secured to an outer surface of the electrode transition section.

6. The electrode arrangement according to claim 1, wherein the additional section of the electrode array comprises all of the electrode array contained within the electrode storage device.

7. The electrode arrangement according to claim 1, wherein the additional section of the electrode array comprises a fractional sub-portion of the electrode array contained within the electrode storage device.

8. The electrode arrangement according to claim 1, wherein the electrode storage device is configured to be controllable after being surgically implanted to further insert a plurality of additional sections of the electrode array from the electrode storage device into the patient cochlea in a sequence of incremental steps.

9. A cochlear implant system having an electrode arrangement according to any of claims 1-8.

* * * * *